US006293947B1

(12) United States Patent
Buchbinder

(10) Patent No.: US 6,293,947 B1
(45) Date of Patent: Sep. 25, 2001

(54) DISTRACTION OSTEOGENESIS DEVICE AND METHOD

(76) Inventor: Daniel Buchbinder, 2 Well House Close, Mamaroneck, NY (US) 10543

(*) Notice: Subject to any disclaimer, the term of this patent is extended or adjusted under 35 U.S.C. 154(b) by 0 days.

(21) Appl. No.: 09/494,134

(22) Filed: Jan. 28, 2000

(51) Int. Cl.[7] ................................. A61B 17/66
(52) U.S. Cl. .......................................... 606/57
(58) Field of Search .................. 606/57, 58, 90, 606/105, 60, 61, 62, 63, 71

(56) References Cited

U.S. PATENT DOCUMENTS

| 3,547,114 | * | 12/1970 | Hoboush | 606/71 |
| 5,364,396 | * | 11/1994 | Robinson et al. | 606/57 |
| 5,672,177 | * | 9/1997 | Seldin | 606/71 |
| 5,718,705 | * | 2/1998 | Sammarco | 606/60 |
| 5,785,713 | * | 7/1998 | Jobe | 606/69 |
| 5,961,524 | * | 10/1999 | Crombie | 606/105 |
| 5,993,448 | * | 11/1999 | Remmler | 606/57 |

* cited by examiner

Primary Examiner—Jeffrey A. Smith
Assistant Examiner—Eduardo C. Robert
(74) Attorney, Agent, or Firm—Michael G. Petit

(57) ABSTRACT

A device and method for performing distraction osteogenesis. The distraction osteogenesis device, in accordance with the present invention, is modular in construction, and has at least two bioabsorbable footplates having screw or rivet holes therein and an extendable member therebetween. The extendable member is used to change the distance between the footplates. When performing the distraction osteogenesis procedure, the footplates are affixed to the bone on either side of an osteotomy/fracture by means of bioabsorbable screws or rivet bone fasteners. The footplates are connected to one another by the extendable member which spans the osteotomy site and stabilizes the bone segments comprising the osteotomy/fracture. Following implantation of the distractor, the extendable member is periodically elongated to incrementally separate the segments of the bone affixed to the respective footplates. Osteogenesis within the osteotomy site is sustained as the juxtaposed ends of the bone segments incrementally separate. When the bone attains a desired length and/or curvature, further elongation of the distractor is discontinued and the newly formed bone is permitted to harden. The extendable member is disconnected from the footplates and surgically explanted. The bioabsorbable footplates and the bioabsorbable screws or rivets affixing the footplates to the bone are not disturbed during explantation of the extendable member and are absorbed by the body over time. The bioabsorbable footplates may be adapted for use with a variety of extendable members.

5 Claims, 2 Drawing Sheets

DISTRACTION OSTEOGENESIS DEVICE AND METHOD

BACKGROUND OF THE INVENTION

1. Field of the Invention

A device and method for elongating a bone, and, more particularly, a modular distractor comprising a extendable member having an adjustable length and absorbable footplates releasably affixed to opposing ends thereof.

2. Prior Art

The general idea of using distraction osteogenesis to elongate bone was reported as early as 1954. Although the technique offered important advantages over prior art methods of bone elongation such as autogenous bone grafting, the technique received relatively little attention in the literature until recently. Ilizarov et al., in U.S. Pat. No. 4,615,338, discloses an apparatus for bone compression or elongation. Muschler, et al., in U.S. Pat. No. 5,429,638, disclose a intermedullary inplant useful for elongating a bone. Other patents disclosing extendable, implantable distraction devices include U.S. Pat. Nos. 5,129,903, 5,364,396, 5,976,142, 5,902,304, 5,873,715 and 5,810,812.

When a bone is broken to enable the controlled mechanical separation of juxtaposed ends of the broken bone, the growth of new bone therebetween (osteogenesis) occurs and may be used to elongate and/or reshape the bone. A distraction osteogenesis device has at least two footplates having screw holes therein and an extendable member therebetween providing means for changing the distance between the footplates. In the performance of the distraction osteogenesis procedure, at least two footplates are affixed to the bone on either side of a fracture by means of screws. The footplates are connected to one another by the extendable member, at least a portion of which spans the fracture site and provides means for stabilizing the osteotomized bony fragments. The footplates and extendable member are collectively referred to as a distractor.

Following implantation of the distractor, the extendable member is periodically manipulated to incrementally separate the bones affixed to the respective footplates. Osteogenesis is sustained within the fracture site as the juxtaposed ends of the bone incrementally separate. When the bone attains a desired length and/or curvature, further elongation of the distractor is discontinued and the newly formed bone is permitted to harden. The distractor is then surgically explanted by unscrewing the footplates from the bone.

The process of distraction osteogenesis begins when a distraction force is applied to a healing callus which joins divided bone segments, and continues for as long as the bone is stretched. The distraction force applied to the bone also creates tension in the surrounding soft tissue. The tension on the bone-associated soft tissue initiates a sequence of adaptive changes, collectively referred to as distraction histogenesis. Thus, skin, fascia, muscle, blood vessels, nerves and tendons undergo distraction histogenesis concurrently with osteogenesis and the adaptive changes in these tissues help to support the bone during and after distraction osteogenesis. It is, therefor, important avoid disturbing such soft tissue when the procedure is completed.

A common feature of prior art distractor devices employed for osteogenic bone elongation include means for rigidly attaching opposing ends of an extendable member to a surgically severed bone (i.e. a bone having an osteotomy) such that the extendable member straddles the osteotomy. The means for attaching the distractor to the bone, or "footplates", comprise plates generally resembling bone plates, having screw holes therein and means thereon for attaching an extendable member thereto. Such footplates are fabricated from a biocompatible metal such as titanium, stainless steel or cobalt chrome alloy. Upon completion of distraction osteogenesis, the footplates must be surgically removed. The trauma of an additional surgical procedure for the explantation of the distractor includes possible damage to adjacent vital structures, swelling, risk of infection and the need (usually) to subject the patient to a general anesthesia. Thus, there remains a need for an osteogenesis distractor device which eliminates the need for a second surgical procedure to explant the distractor footplates.

SUMMARY OF THE INVENTION

It is a first object of the invention to provide a osteogenesis distraction device for surgical implantation which minimizes trauma to the tissues comprising the operative site.

It is a second object of the invention to provide a method for performing a distraction osteogenesis procedure wherein damage to tissues comprising the operative site is minimized.

It is a further object of the invention to provide a device for performing distraction osteogenesis which may be explanted following completion of the procedure with minimal trauma to the bone and the bone-associated soft tissue which has undergone distraction histogenesis.

It is yet another object of the invention to provide a device which may be used for applying an axially directed compressive force to a fractured bone.

The above objectives are met by a distractor having modular construction and comprised of at least two bioabsorbable footplates which are operable for anchoring the distractor to a bone. The bioabsorbable footplates are affixed to the bone by bioabsorbable bone fastener means such as bioabsorbable screws or rivet bone fasteners. In the event that the distractor must be explanted, either during the procedure or after bone elongation is complete, the footplates, being bioabsorbable and separable from the distractor, are disconnected from the distractor and remain in situ. Since explantation of footplates is avoided, trauma to the operative site is minimized.

The features of the invention believed to be novel are set forth with particularity in the appended claims. However the invention itself, both as to organization and method of operation, together with further objects and advantages thereof may be best be understood by reference to the following description taken in conjunction with the accompanying drawings in which:

BRIEF DESCRIPTION OF THE PREFERRED EMBODIMENTS

The term "bioabsorbable material" or "bioabsorbable", as used herein, means that the referenced material is biocompatible, and that at least a portion of the material is either excreted or assimilated by the body following implantation therewithin, Although the description of the preferred embodiments of the invention presented herein are directed to embodiments of the device which are operable for performing distraction osteogenesis, it should be understood that replacement of the extendable member of the device with a retractable member, provides a device operable for applying a compressive force to an osteotomy site which can be used to accelerate healing of a fracture.

Figure 1:
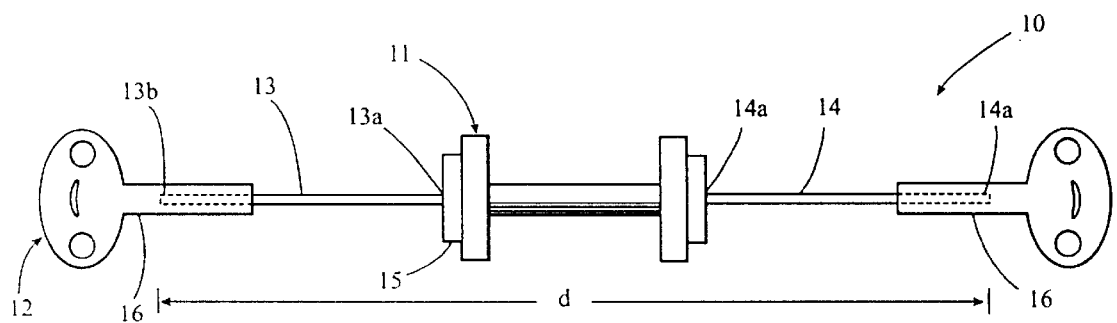
FIG. 1 is a plan view of a modular distraction device illustrating modular construction.
Figure 2:
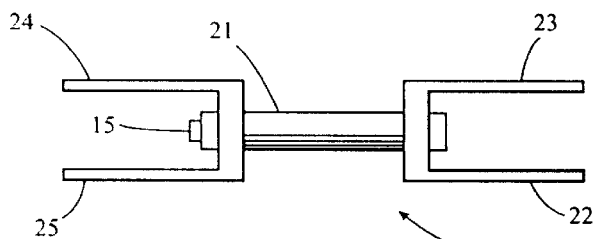
FIG. 2 is a plan view illustrating an embodiment of a distractor in accordance with the present invention wherein the extendable or compressive member of the device includes multiple legs, all of which may be attached to footplates.

Turning now to FIG. 1, a distractor, indicated at numeral 10 includes a extendable member 11 and two footplates 12. The extendable member 11 has two legs 13 and 14, the proximal ends 13a and 14a of which legs are affixed thereto. The extendable member 11 includes mechanical extension means 15 operable for varying the distance d between the distal ends 13b and 14b of the legs 13 and 14 respectively. Exemplary of such extension means are Glen-Ross screws and compression/extension devices such as tumbuckles, vises or clamps, comprising a double-threaded rotatable screw having two threaded members slidably mounted thereon. The distal ends 13b and 14b of the legs are dimensioned to fit snugly within a hollow extension tube 16, which tube 16 is integral with the footplate 12. FIG. 2 shows a distractor 20 comprising an extendable member 21 having four legs 22–25 extending laterally therefrom, useful for applying symmetric tension (or compression) to juxtaposed bone segments comprising an osteotomy.

Figure 3:
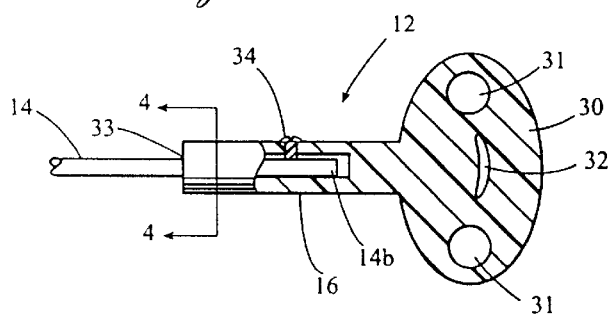
FIG. 3 is a top partially cutaway cross-sectional view of a bioabsorbable footplate adapted for attachment to a leg of an extendable member of a distractor device in accordance with the present invention.

FIG. 3 is a top plan view of a bioabsorbable footplate 12 having unitary construction in accordance with a unitary embodiment of the present invention, illustrating particular features of the present footplate deemed to provide advantages over prior art footplates. The footplate 12 is of unitary construction and fabricated from a bioabsorbable polymeric material. Examples of suitable bioabsorbable materials include polymers or copolymers of lactide, glycolide, caprolactone, polydioxanone, trimethylene carbonate, polyorthoesters and polyethylene oxide. Suitable bioabsorbable bone fasteners such as screws and rivets suitable for attaching a footplate to a bone are commercially available.

The unitary footplate 12 has a bone attachment portion 30 having a hollow extension tube 16 integral therewith. The bone attachment portion 30 includes at least one, and more preferably two, screw holes 31 therein, dimensioned to receive a bone fastener such as a screw or rivet. The bone attachment portion 30 is elastically flexible and can be made to conform to the curvature of the bone surface. A slit 32 disposed between the screw holes facilitates bending of the bone attachment portion 30 thereby enabling the attachment portion 30 to substantially conform to the contour presented by the surface of a bone.

Figure 4:
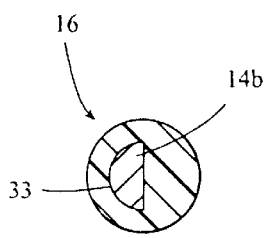
FIG. 4 is a cross-sectional view of the extension tube in accordance with the footplate of FIG. 3, taken along section line 4—4.
Figure 5:
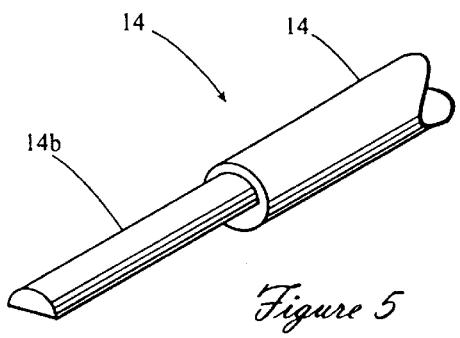
FIG. 5 is a perspective view of an embodiment of a leg in accordance with FIGS. 3 and 4 of the present invention.

The hollow extension portion 16 has an axial bore 33 which is dimensioned to accommodate the distal end 14b of a leg 14 inserted therewithin. The hollow extension tube 16 further includes leg attachment means 34 operable for reversibly locking the distal end 14b of the leg 14 within the axial bore 33. The axial bore 33 may have any one of a variety of cross-sectional shapes, one of which is the semi-circle shown in FIG. 4. With reference to FIG. 4, the distal end 14b of the leg 14 and hollow extension portion 16, viewed along section line 4—4 of FIG. 3, is particularly suitable for use when the leg attachment means 34 is a set screw. FIG. 5 is a perspective view of the distal end 14b of the leg 14 illustrating a semicircular cross-section used in the unitary embodiment of the footplate shown in FIGS. 3 and 4. In the event that the distal end 14b of the leg 14 is threaded (not shown), the set screw leg attachment means 34 would most preferably be replaced by a matingly pitched thread tapped within the cylindrical axial bore 33 of the extension portion 16, presenting a concentric circular cross-section (not shown) at section line 4—4.

The distal end 14b of the legs 14 may be affixed to the bioabsorbable footplate 12 by insertion molding to provide a hybrid embodiment of a footplate useful for performing distraction osteogenesis. Such a hybrid embodiment of a footplate is shown in top plan view at 60 in FIG. 6. The hybrid footplate 60 is comprised of a non-bioabsorbable leg 14 integrally attached to a unitary bioabsorbable footplate 12. The hybrid footplate 60 is of modular construction, having a non-bioabsorbable leg 14 affixed to a unitary bioabsorbable footplate 12. FIG. 7 is a top cross-sectional view of the hybrid embodiment of the bioabsorbable footplate 60 shown in FIG. 6. A preferable shape for the distal end portion 14b of the leg 14 is conical; the leg 14 being flared inwardly adjacent to the distal end 14b of the leg.

Figure 6:
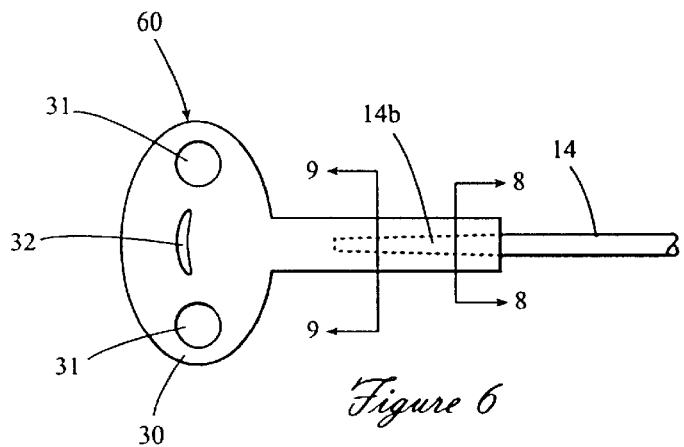
FIG. 6 is a top plan view of a hybrid embodiment of a footplate in accordance with the present invention wherein a non-bioabsorbable leg is integrally attached to a bioabsorbable footplate.
Figure 7:
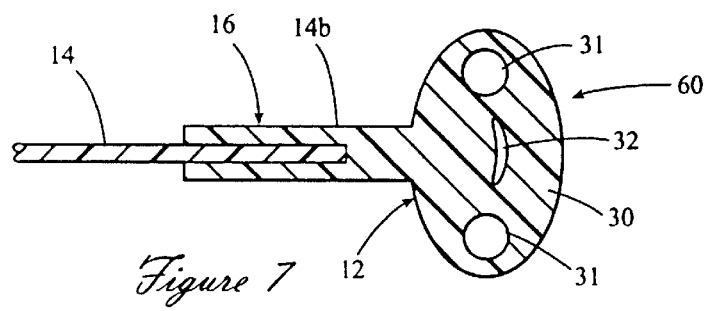
FIG. 7 is a top cross-sectional view of a hybrid embodiment of a bioabsorbable footplate in accordance with FIG. 6 wherein a non-bioabsorbable leg is integrally attached to a bioabsorbable footplate.
Figures 8, 9:
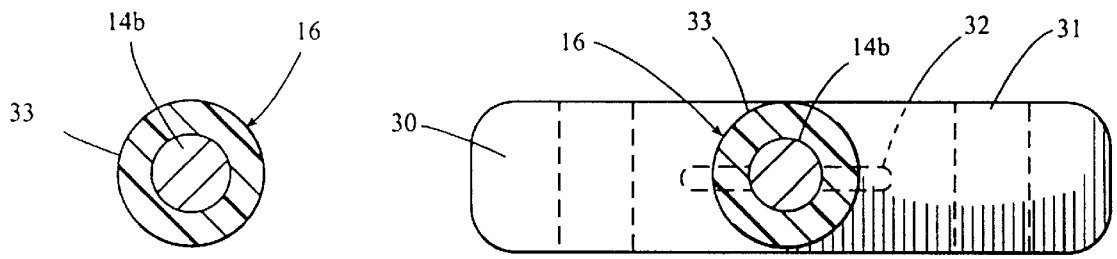
FIG. 8 is a cross-sectional view of a hybrid footplate in accordance with FIG. 6 viewed along section line 8—8.
FIG. 9 is a cross-sectional view of a hybrid footplate in accordance with FIG. 6 viewed along section line 9—9.
Figure 10:
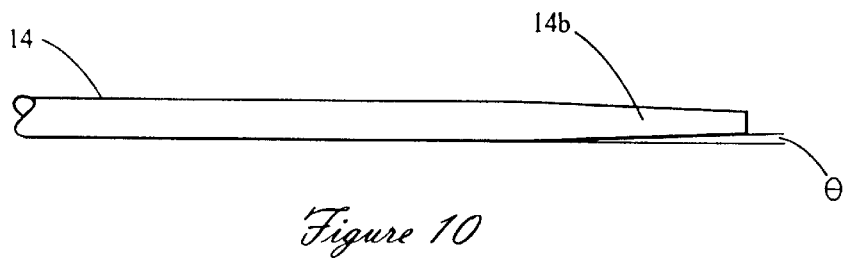
FIG. 10 is an enlarged side view of a leg used to form a hybrid footplate as shown in FIGS. 6–9, illustrating the conical taper of the distal end of the leg.

FIGS. 8 and 9 are cross-sectional views of the hybrid footplate 60, shown in FIG. 6, viewed along section lines 8—8 and 9—9 respectively. In the hybrid embodiment of the footplate 60, both the axial bore 33 of the hollow extension portion 16 and the distal end 14b of the leg have a circular transverse cross-section as illustrated in FIGS. 8 and 9. FIG. 10 is an enlarged side elevational view of the leg 14 of the hybrid footplate 60, as shown in FIGS. 6–9, illustrating the conical taper of the distal end portion 14b of the leg 14. Suitable values for the angle θ, the angle of convergence of the conical distal end portion 14b, range between 1 and 5 degrees and is preferably around 3 degrees.

Referring back to FIG. 7, the bioabsorbable portion 30 of the hybrid footplate 60 is molded around the distal end 14b of the leg 14 to conform to the conical shape thereof. Following implantation, bioabsorbtion of the wall of the axial bore 33 separates the footplate from the leg 14. During explantation of the distraction osteogenesis device, the conical taper θ enables the leg 14 to be removed from within the partially degraded, bioabsorbable axial bore 33 of the bioabsorbable bone attachment portion 30 of the hybrid footplate 60 by applying gentle traction to the opposing proximal end 14a of the leg 14.

A method for performing distraction osteogenesis using a distractor device comprised of bioabsorbable footplates in accordance with the present invention, is as follows. First a patient is anesthetized and a bone to be elongated or reformed is exposed by surgical dissection. Depending on the desired result, the optimal location for the osteotomy is determined and performed, severing the bone. A sterile extendable member having at least two opposing legs, and at least two sterile, bioabsorbable footplates comprised of a bone attachment portion having screw holes therein and a hollow extension tube having an axial bore and being integral with the bone attachment portion are presented.

Holes are drilled in one segment of the severed bone and a bioabsorbable footplate is attached to the bone segment using bioabsorbable bone fasteners. The distal end of one leg of the extendable member is contoured to the desired shape so that the metallic component of the device is outside of the surgical site. The distal end of one leg of the extendable member is inserted into the axial bore of the extension tube on the footplate and locked therewithin by leg attachment means. Next, the distal end of an opposing leg of the extendable member, also contoured, is inserted into the axial bore of a second footplate and holes are drilled in the second segment of severed bone and the second bioabsorbable footplate attached to the second segment by bioabsorbable bone fasteners. The distal end of the opposing leg of the extendable member is locked within the axial bore of the hollow extension portion of the second footplate by leg attachment means. Soft tissue dissected in order to expose the bone may be reattached to the bone and the wound closed.

Means for extending or retracting (i.e. activating) the distractor by manipulating the extendable member may be accessed in a variety of ways. In many instances, the means for distractor extension is externally accessible, projecting from the skin or oral mucosa through a partially closed wound. In other instances, it may be preferable to insert an extension tool under the skin to activate (extend or shorten) the distractor device. It may be possible, in certain instances, to hydraulically activate the distractor via transdermal injection of a biocompatible fluid such as saline or silicone oil into an implanted subcutaneous reservoir in fluid communication with the extendable member.

When the distraction osteogenesis procedure is complete, it is desirable to remove the distractor. The advantage of the present distractor is that only the extendable, non-submerged member need be removed. The legs of the extendable member are disconnected from the footplates and the extendable member removed. The leg explant site is then allowed to heal or the wound can be surgically closed. The footplates, which are attached to the bone and embedded in soft tissue, as well as the bone fasteners, remain implanted and will be bioabsorbed in due course.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What I claim is:

1. A method for elongating a bone having first and second bone segments separated by a fracture comprising the steps of:
   (a) presenting a sterile bone distraction device in accordance with claim 1; then
   (b) surgically exposing said fracture and a portion of a surface on the first and second bone segments; then
   (c) drilling a hole in said first and second bone segments; then
   (d) attaching the first footplate to the first bone segment and the second footplate to the second bone segment by bioabsorbable bone fastener means and wherein the telescopic member spans the fracture; then
   (e) closing the wound thereby implanting the distraction device within the body; then
   (f) increasing the distance between the first and and second bone segments by the percutaneous adjustment of the adjustment means; then
   (g) repeating step (f) until the desired elongation is attained; then
   (h) surgically exposing and detaching the telescopic member from the first and second footplates and explanting the telescopic member while leaving the first and second bioabsorbable footplates attached to the first and second bone segments; then
   (i) closing the wound.

2. A surgically implantable distraction device operable for distracting a first bone segment spaced by a fracture from a second bone segment comprising:
   (a) a first bioabsorbable footplate;
   (b) a second bioabsorbable footplate;
   (c) bioabsorbable bone fastener means operable for attaching said first absorbable footplate to the first bone segment and said second bioabsorbable footplate to the second bone segment; and
   (d) a rigid telescopic member having a first end attached to said first bioabsorbable footplate and a second end attached to said second bioabsorbable footplate, and a distance between said first and second ends, said telescopic member further comprising adjustable means operable for incrementally changing said distance between said first end and said second end of said telescopic member and wherein said telescopic member is metallic.

3. The device in accordance with claim 2 wherein said first and second bioabsorbable footplates comprise a bioabsorbable material selected from the group consisting of polymers or copolymers of lactide, glycolide, caprolactone, polydioxanone, trimethylene carbonate, polyorthoesters and polyethylene oxide.

4. A surgically implantable bone compression device operable for compressing a fracture separating a first bone segment from a second bone section comprising:
   (a) a first bioabsorbable footplate;
   (b) a second bioabsorbable footplate;
   (c) bioabsorbable bone fastener means operable for attaching said first absorbable footplate to the first bone segment and said second bioabsorbable footplate to the second bone segment; and
   (d) a rigid telescopic member having a first end attached to said first bioabsorbable footplate and a second end attached to said second bioabsorbable footplate, and a distance between said first and second ends, said telescopic member further comprising adjustable means operable for incrementally changing said distance between said first end and said second end of said telescopic member and wherein said telescopic member is metallic.

5. The device in accordance with claim 4 wherein said first and second bioabsorbable footplates comprise a bioabsorbable material selected from the group consisting of polymers or copolymers of lactide, glycolide, caprolactone, polydioxanone, trimethylene carbonate, polyorthoesters and polyethylene oxide.

* * * * *